United States Patent [19]

Scholz

[11] Patent Number: 5,292,413
[45] Date of Patent: Mar. 8, 1994

[54] CATHOLYTE FOR THE KARL FISCHER COULOMETRIC WATER DETERMINATION

[75] Inventor: Eugen Scholz, Garbsen, Fed. Rep. of Germany

[73] Assignee: Riedel-De Haen Aktiengesellschaft, Seelze, Fed. Rep. of Germany

[21] Appl. No.: 909,155

[22] Filed: Jul. 6, 1992

[30] Foreign Application Priority Data

Jul. 19, 1991 [DE] Fed. Rep. of Germany ....... 4123976

[51] Int. Cl.$^5$ ........................................... G01N 27/26
[52] U.S. Cl. .......................... 204/153.22; 204/153.23; 204/405; 436/42; 252/62.2
[58] Field of Search .............. 204/405, 153.22, 153.23; 436/42; 252/62.2

[56] References Cited

U.S. PATENT DOCUMENTS

| | | | |
|---|---|---|---|
| 4,378,972 | 4/1983 | Scholz | 436/42 |
| 4,429,048 | 1/1984 | Scholz | 436/42 |
| 4,550,083 | 10/1985 | Fischer et al. | 436/42 |
| 4,703,014 | 10/1987 | Fischer et al. | 436/39 |
| 4,740,471 | 4/1988 | Scholz | 204/153.22 |
| 5,102,804 | 4/1992 | Fischer et al. | 436/42 |
| 5,139,955 | 8/1992 | Scholz | 436/42 |

FOREIGN PATENT DOCUMENTS

| | | |
|---|---|---|
| 0086994 | 8/1983 | European Pat. Off. . |
| 0127740 | 12/1984 | European Pat. Off. . |
| 0384195 | 8/1990 | European Pat. Off. . |
| 0435122 | 7/1991 | European Pat. Off. . |
| 3407014 | 8/1985 | Fed. Rep. of Germany . |
| 1074686 | of 0000 | France . |
| 722983 | 2/1955 | United Kingdom . |

*Primary Examiner*—John Niebling
*Assistant Examiner*—Bruce F. Bell
*Attorney, Agent, or Firm*—Connolly and Hutz

[57] ABSTRACT

The present invention relates to a catholyte for the Karl Fischer coulometric water determination, which is characterized in that it is composed of a solution of one or more salts of an organic nitrogen base and acid in a solvent.

10 Claims, No Drawings

CATHOLYTE FOR THE KARL FISCHER COULOMETRIC WATER DETERMINATION

The present invention relates to a catholyte for the Karl Fischer coulometric water determination, which catholyte is characterised by a content of a salt of an organic nitrogen base.

A Karl Fischer volumetric titration reagent contains, for example, methanol, sulphur dioxide, pyridine (Py) and iodine as reactive constituents. The water determination is in that case based on the so-called Karl Fischer reaction:

$$CH_3OH + SO_2 + Py \rightarrow (PyH)\ SO_3CH_3$$
$$H_2O + I_2 + (PyH)\ SO_3CH_3 + 2Py \rightarrow (PyH)$$
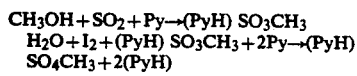
$$SO_4CH_3 + 2(PyH) \qquad\qquad I$$

In this process, a salt of methylsulphurous acid is first formed after the first reaction step, which salt is then oxidised after the second reaction step by iodine with the consumption of an equivalent quantity of water.

The Karl Fischer titration can be carried out in the form of a coulometric determination in a specially constructed cell. In the latter, a smaller cathode space (normally about 5 ml) is inserted into a larger anode space (normally about 100 ml) and separated from the latter by a membrane (see, for example, E. Scholz, Karl-Fischer-Titration, Springer-Verlag 1984, pages 19-20).

"Consumed" Karl Fischer solutions, i.e. Karl Fischer solutions in which the iodine has already been reduced to iodide, are frequently used as reagent solutions. The iodine necessary for the water determination is produced by anodic oxidation of the iodide. The water content can then be calculated from the current consumption for this oxidation reaction, i.e. the anode reaction must proceed with 100% current efficiency.

The reagent solution is used both for the anode space and for the cathode space, but is frequently modified, for instance by adding other solvents. For example, carbon tetrachloride is frequently used in the cathode space.

A disadvantage of the reagent solutions mentioned is that, when current flows, the sulphur dioxide (possibly in bound form as methyl sulphite) is cathodically reduced to lower sulphur compounds. These compounds migrate through the membrane into the anode space under the influence of the electric field, are oxidised there by iodine and consequently simulate water contents (Analytical Sciences, April 1991, Volume 7, pages 299-302). The water contents found are therefore always too high. The error depends on the quantity of water analysed since the concentration of the oxidisable components first rises and then falls again. The formation of the reducible components may be affected by other substances. For example, it increases considerably if guanidine is present (German Offenlegungsschrift 34 07 014). Although the carbon tetrachloride already mentioned above reduces the formation of oxidisable components, as a halogenated hydrocarbon it is increasingly less acceptable.

The object of the present invention is to disclose a catholyte for the Karl Fischer coulometric water determination which has a higher measurement accuracy than the catholytes hitherto known and at the same time gets by without halogenated hydrocarbons.

The present invention relates to a catholyte for the Karl Fischer coulometric water determination, characterised in that it is composed of a solution of one or more salts of an organic nitrogen base and acid in a halogen-free solvent.

Suitable organic nitrogen bases are, for example, primary, secondary or tertiary aliphatic amines containing 1 to 12 carbon atoms per alkyl group, it being possible for the alkyl groups also to be substituted by, for example, a hydroxyl group, primary, secondary or tertiary cycloaliphatic amines containing 3 to 8 carbon atoms per cycloalkyl group, alkylenediamines containing 1 to 8 carbon atoms, cyclic amines containing 3 to 8 ring members, or aromatic amines containing 5 or 6 ring members.

Preferred organic nitrogen bases are, for example, methylamine, diethylamine, propylamine, octylamine, trimethylamine, dimethyldodecylamine, cyclohexylamine, dicyclohexylamine, aminoethanol, diethanolamine, triethanolamine, N,N-dibutylethanolamine, ethylenediamine, hexamethylenediamine, morpholine, piperidine, pyridine, imidazole and triazines.

Both organic and inorganic acids are suitable as acids which form salts as claimed with the organic nitrogen bases mentioned.

Preferred acids are, for example, hydrochloric acid, hydrobromic acid, hydroiodic acid, sulphuric acid, methylsulphuric acid, orthophosphoric acid, benzolic acid, salicylic acid, propionic acid and decylcarboxylic acid.

In particular, methanol and 1-propanol are preferred as solvents for the salts as claimed. However, other halogen-free solvents, such as, for example, 2-methoxyethanol, can also be used. The concentration of the salts as claimed in the catholytes according to the invention is preferably 0.1-10 mol/l, particularly preferably 1-5 mol/l.

The catholytes according to the invention may contain one or more salts. In the latter case, the mixing ratios of the salts are not at all critical and can be varied as desired.

It is possible to dehydrate the catholytes according to the invention with conventional Karl Fischer titrating solution before use or to add the components of the conventional Karl Fischer solution based on sulphur dioxide directly.

The catholytes according to the invention are poured into the cathode space of the Karl Fischer coulometer, whereas a conventional anolyte is poured into the anode space. A conventional anolyte is understood to mean a solution containing base, sulphur dioxide and iodide, such as the solution of Example 8.

During the water determination (i.e. during the electrolysis), only hydrogen, which escapes from the cell, is liberated at the cathode with the catholyte according to the invention. It is unable either to reach the anode space or to be oxidised by iodine under the conditions of the Karl Fischer titration. This prevents any disturbance of the Karl Fischer titration.

A special form of Karl Fischer coulometry is the membrane-free cell, which contains only one chamber, with the result that the cathode reaction and the anode reaction proceed in the same reagent solution (E. Scholz, Laborpraxis 13, 526-531 (1989)). For this purpose, the catholyte according to the invention may be mixed with a conventional anolyte as defined above. At the same time, the mixing ratio may vary within wide limits, a minimum concentration, on the one hand, of 0.2 mol/l of sulphur dioxide and a minimum concentration, on the other hand, of 0.1 mol/l of the salt as claimed being necessary.

EXAMPLE 1

Catholyte composed of 30.8 g of diethylamine hydrobromide (0.2 mol) in 100 ml of methanol.

EXAMPLE 2

283 g of diethanolamine hydrochloride (2 mol) in methanol dissolved to form a total volume of 1 l.

EXAMPLE 3

Catholyte composed of 64.8 g of diethanolamine methylsulphate (0.3 mol) and 139 g of diethanolamine hyroiodide (0.6 mol in 1 l of methanol).

EXAMPLE 4

Catholyte composed of 22.1 g of cyclohexylamine benzoate (0.1 mol) in 100 ml of methanol.

EXAMPLE 5

Catholyte composed of 156 g of N,N-dibutylethanolamine salicylate (0.5 mol) in 1 l of 1-propanol.

EXAMPLE 6

123 g of morpholine hydrochloride are dissolved in 1 l of methanol. Then 14 g of imidazole (0.2 mol) are added and 6.4 g of sulphur dioxide (0.1 mol) are introduced into the solution. Then solid iodide is added while stirring until it is no longer completely reduced. In this way, the catholyte is dried.

EXAMPLE 7

Catholyte composed of 167 g of triazine dihydroiodide (0.5 mol) in 1 l of methanol.

EXAMPLE 8

231 g of pyridine hydrochloride (2 mol) are dissolved in 1 l of methanol. This solution is mixed with 1 l of a conventional reagent which is composed of 1.8 mol/l of pyridine, 1 mol/l of sulphur dioxide, 0.05 mol/l of pyridine hydroiodide and methanol as solvent. This mixture is suitable both as catholyte in the Karl Fischer cell containing a membrane and as a single component reagent in the membrane-free cell.

APPLICATION EXAMPLE 100 ml of a conventional coulometric reagent composed of 1.3 mol/l of diethanolamine, 1.0 mol/l of sulphur dioxide, 0.1 mol/l of iodide and methanol as solvent were poured into the anode space of a commercially available Karl Fischer coulometer (coulometer supplied by Kyoto Electronic, Japan, Model MKC 210). 5 ml of the catholyte from Example 2 were poured into the cathode space. Four portions of 25 mg of water in each case were added consecutively to the same solution and analysed. The values
25.08 mg
24.92 mg
25.14 mg and
25.11 mg
were found.

COMPARISON EXAMPLE

The measurements of the application example were repeated, with the difference that the cathode space contains the same conventional coulometric reagent as the anode space. The following values were obtained:
24.82 mg
25.57 mg
26.25 mg
25.56 mg

I claim:

1. Catholyte for the Karl Fischer coulometric water determination comprising a solution of one or more salts of an organic nitrogen base and acid in a non-halogenated solvent and being essentially free of sulphur dioxide.

2. Catholyte according to claim 1, characterized in that the organic nitrogen bases are primary, secondary or tertiary aliphatic amines containing 1 to 12 carbon atoms per alkyl group, wherein the alkyl groups are unsubstituted or optionally substituted by a hydroxyl group, primary, secondary or tertiary cycloaliphatic amines containing 3 to 8 carbon atoms per cycloalkyl group, alkylenediamines containing 1 to 8 carbon atoms, cyclic amines containing 3 to 8 ring members, or aromatic amines containing 5 or 6 ring members.

3. Catholyte according to claim 1 characterized in that the organic nitrogen base is methylamine, diethylamine, propylamine, octylamine, trimethylamine, dimethyldodecylamine, cyclohexylamine, dicyclohexylamine, aminoethanol, diethanolamine, triethanolamine, N,N-dibutylethanolamine, ethylenediamine, hexamethylenediamine, morpholine, piperidine, pyridine, imidazole or triazines.

4. Catholyte according to claim 1 characterized in that the acid is hydrochloric acid, hydrobromic acid, hydroiodic acid, sulphuric acid, methylsulphuric acid, orthophosphoric acid, benzolic acid, salicylic acid, propionic acid or decylcarboxylic acid.

5. Catholyte according to claim 1 characterized in that the solvent is methanol or 1-propanol.

6. Catholyte according to claim 1 characterized in that it is dehydrated with a Karl Fischer solution.

7. A method for the coulometric determination of water by the Karl Fischer reaction wherein the catholyte according to claim 1 is used for the Karl Fischer coulometric water determination.

8. Catholyte for the Karl Fischer coulometric water determination consisting essentially of a solution of one or more salts of an organic nitrogen base and acid in a non-halogenated solvent.

9. Catholyte according to claim 1, wherein said salts are in a concentration from 0.1 to 10 mol/l.

10. Catholyte according to claim 1, wherein said salts are in a concentration from 1 to 5 mol/l.

* * * * *